8/14/84 XR 4,465,802

United States Patent [19]

Dennen et al.

[11] Patent Number: 4,465,802

[45] Date of Patent: Aug. 14, 1984

[54] PROCESS FOR TREATING FURRED ANIMAL PELTS AND/OR FUR

[75] Inventors: William M. Dennen, Ringwood, N.J.; Mary E. Turney, Briarcliff Manor, N.Y.

[73] Assignee: Union Carbide Corporation, Danbury, Conn.

[21] Appl. No.: 436,669

[22] Filed: Oct. 26, 1982

[51] Int. Cl.$^3$ .................... A61K 7/06

[52] U.S. Cl. .................... 524/395; 8/94.14; 8/94.15; 8/94.18; 8/107; 8/404; 106/170; 252/8.57; 424/70

[58] Field of Search .................... 524/395; 8/404, 94.14, 8/94.15, 94.18, 107; 106/170; 252/8.57; 424/70

[56] References Cited

U.S. PATENT DOCUMENTS

| | | | |
|---|---|---|---|
| 3,472,840 | 10/1969 | Stone et al. | 536/31 |
| 3,917,817 | 11/1975 | Vanlerberghe et al. | 528/405 |
| 3,958,581 | 5/1976 | Abegg et al. | 424/70 |
| 4,009,255 | 2/1977 | Kalopissis et al. | 424/70 |
| 4,165,367 | 8/1979 | Chakrabarti | 424/70 |
| 4,197,865 | 4/1980 | Jacquet et al. | 424/70 |
| 4,315,912 | 2/1982 | Kalopissis et al. | 424/70 |
| 4,318,901 | 3/1982 | Ishida et al. | 424/70 |
| 4,321,348 | 3/1982 | Jacquet et al. | 424/70 |
| 4,364,837 | 12/1982 | Pader | 424/70 |

*Primary Examiner*—Ronald W. Griffin
*Attorney, Agent, or Firm*—Donald M. Papuga; Henry H. Gibson

[57] ABSTRACT

Described herein is a composition for treating furred animal pelts and/or fur, which composition comprises a water soluble cationic polymer, a cationic surfactant, and water.

12 Claims, No Drawings

PROCESS FOR TREATING FURRED ANIMAL PELTS AND/OR FUR

BACKGROUND OF THE INVENTION

This invention is directed to a composition for treating furred animal pelts and/or fur, which composition comprises a water soluble cationic polymer, a cationic surfactant, and water.

The processing of furred animal pelts requires the extensive use of water or other aqueous treating or cleaning solutions. This occurs not only in the initial soaking and tanning of the raw or dried pelts, but also occurs in the subsequent processing operations which may include stretching and shaping of the pelts and the bleaching or dyeing of the fur thereon. In all such processing, it is important to secure penetration of the pelt and the fur by the water or aqueous solution utilized. After such penetration, the water or other aqueous constituents which have penetrated both the fur and skin portions of the pelt must be removed, and the pelt dried. During such processing, the wet pelt is very soft and pliable, and is easily worked. Removal of the water or aqueous treating solution, and the subsequent drying of the pelt causes the pelt to lose much of its softness and pliability. The pelt, on drying, becomes less flexible, the appearance of the fur deteriorates, and the bond or union between the skin and the fur hairs is weakened frequently causing excessive shedding of the fur hairs.

Surface treatments have been used in an attempt to restore the appearance of the fur. Such treatments however, at best, are temporary expedients and do not restore or maintain the natural appearance of the fur.

Also, the successive wetting, dyeing, and drying of fur pelts causes a progressive deterioration in the appearance of the fur portion. The fur loses its natural texture since it is harsh to the touch and it also has an unkempt appearance.

Therefore, it is an object of the present invention to provide a novel composition of matter for treating furred animal pelts and/or fur to restore their natural appearance and feel.

Also, it is another object of this invention to provide a novel composition for providing furs with a high gloss or shine essentially without the appearance of oiliness.

DESCRIPTION OF THE INVENTION

It has now been found that the composition of this invention of a combination of a water soluble cationic polymer, cationic surfactant and water, when used to treat furred animal pelts and/or furs provides the fur with a high gloss and shine. After dying the animal pelt or fur, treatment with the composition of this invention helps restore the fur or pelts to their natural condition. In addition, treatment of the pelt with the present composition helps maintain a desirable moisture level in the animal skin.

The composition of this invention preferably contains, in addition to the water soluble cationic polymer, cationic surfactant, and water, one or more of a primary emulsifier, a secondary emulsifier, a surface active antistatic agent, and a preservative.

The cationic polymers usefully employed in the compositions of the present invention belong to a class of well known compounds. In a general fashion this term "cationic polymers" means those polymers exhibiting in their principal chain or in the substituted form, at least one tertiary amine or quaternary ammonium group. Usually the cationic polymers employed in the compositions of the present invention have an average molecular weight between about 1000 and 3,000,000.

Representative cationic polymers which can be used in accordance with the present invention include, especially, the following polymers:

1. The quaternary derivatives of cellulose ether of the formula:

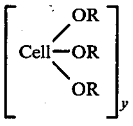

wherein Cell represents the residue of an anhydroglucose unit, y represents a whole number between about 50 and about 20,000, and preferably between about 200 and about 5000, and the radicals R, identical or different, represent a group of the formula:

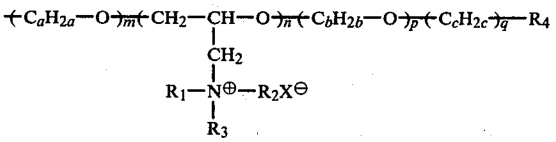

wherein a and b are 2 or 3; c is 1, 2 or 3; m an p are whole numbers from 0 to 10; n is a whole number from 0–3; q is 0 or 1; $R_1$, $R_2$ and $R_3$ each independently represent alkyl, aryl, aralkyl, alkaryl, cycloalkyl, alkoxyalkyl or alkoxyaryl, containing 1–10 carbon atoms and such that the sum of the number of carbon atoms of $R_1$, $R_2$ and $R_3$ varies from 3–12; it being understood that when any one of $R_1$, $R_2$ and $R_3$ is alkoxyalkyl, there are at least two carbon atoms between the oxygen of the alkoxy moiety and the nitrogen atom to which the alkyl moiety is attached; and $X^-$ represents the anionic residue of a mineral or organic acid. $R_4$ is selected from H,

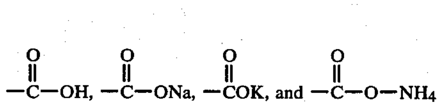

with the proviso that when q is O than $R_4$ is H.

Representative anions designated as $X^\ominus$, include, for instance, chloride, bromide, iodide, sulfate, bisulfate ($HSO_4^-$), $CH_3SO_3^-$, sulfonate, phosphate, acetate and the like.

The average value of n is between about 0.01 and 1 per anhydroglucose unit, and preferably between about 0.1 and 0.5.

The average value of (m+n+p+q) is between about 0.01–4 per unit of anhydroglucose.

Such quaternary derivatives of cellulose ether are described, for instance, in French Pat. No. 1,492,597 as well as in U.S. Pat. No. 3,472,840, incorporated herein by reference.

The quaternary derivatives of cellulose ether can be prepared in accordance with processes described in these two patents, for instance, by etherification and quaternization; these two operations being able to be made in any order or even simultaneously.

The etherification operation effects the fixation on the cellulose chain of a short chain alkyl or hydroxy alkyl substituent having, for example, up to 4 carbon atoms, and preferably an alkyl substituent having 1-3 carbon atoms or a hydroxyalkyl substituent having from 2-4 carbon atoms.

To effect etherification there is employed, preferably, an alkylating agent such as dimethylsulfate, diethyl sulfate, methyl chloride, methyl bromide, ethyl chloride, ethyl bromide or n-propyl chloride; or a hydroxy alkylating agent such as ethylene oxide or propylene oxide.

For the quaternization reaction, there is employed a quaternary halohydrin of the formula:

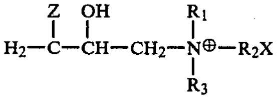

or a quaternary epoxide of the formula

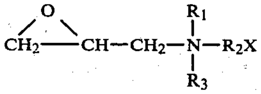

wherein $R_1$, $R_2$ and $R_3$ are defined above, Z is Cl, I or Br, and $X^-$ is an anion and preferably the anion residue of a strong mineral acid.

The radicals R fixed on the anhydroglucose chain can be, for example, the following: H, $-CH_3$, $-C_2H_5$, $-CH_2CH_2OH$, $-(CH_2CH_2O)_s-CH_2OH$ wherein s is 1 or 2.

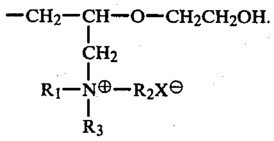

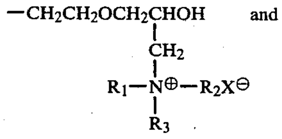

and

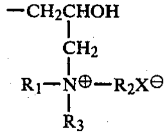

wherein $R_1$, $R_2$ and $R_3$ are defined as above and represent for example methyl or ethyl, with X being, for example, Cl.

When the quaternized polymer of cellulose ether is prepared starting with a cellulose ether, the later is preferably selected from the group consisting of nonionic water soluble cellulose ethers and nonionic water soluble cellulose ethers substituted by a short chain alkyl or hydroxyalkyl. These derivatives are, principally methyl-, ethyl-, or hydroxyethylcellulose.

Representative quaternized derivatives of cellulose ethers usefully employed in the present invention include the commercial product UCARE POLYMER JR sold by Union Carbide Corporation.

2. Copolymers of the formula

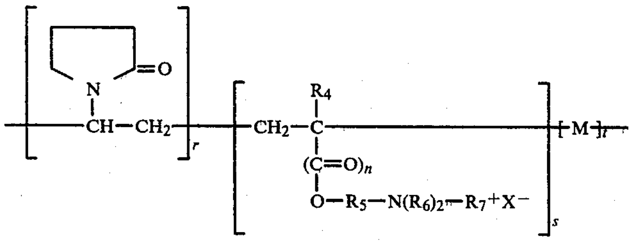

wherein, on the basis of 100 moles of monomer units (i.e. $r+s+t=100$), r is a whole number between 20 and 99, s is a whole number between 1 and 80 and t is a whole number between 0 and 50; $n=0$ or 1; $R_4$ represents hydrogen or methyl; $R_5$ represents

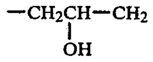

or $C_xH_{2x}$ wherein x is a whole number between 2 and 18; $R_6$ is methyl, ethyl or tert-butyl; $R_7$ is methyl, ethyl or benzyl; $X^-$ represents a chloride, bromide, iodide, sulfate, bisulfate or $CH_3SO_3^-$ anion; and M represents a copolymerizable vinyl monomer unit.

The optionally present copolymerizable vinyl monomer represented by M in the foregoing formula, is a conventional vinyl monomer copolymerizable with N-vinyl pyrrolidone. These vinyl monomers are principally alkyl vinyl ethers wherein the alkyl moiety has preferably from 1-8 carbon atoms, for example, methyl vinyl ether, ethyl vinyl ether, octyl vinyl ether; alkyl esters of acrylic or methacrylic acid, principally those wherein the alkyl moiety has from 1-4 carbon atoms, for instance, methyl acrylate or methyl methacrylate; vinyl aromatic monomers such as stryene and methyl styrene; vinyl esters such as vinyl acetate; vinylidene chloride; acrylonitrile; methacrylonitrile; acrylamide; methacrylamide; vinyl chloride; and alkyl crotonates, wherein the alkyl moiety has, preferably, from 1 to 8 carbon atoms, and the like.

These copolymers are prepared by copolymerization of (1) N-vinylpyrrolidone, (2) the acrylate or methacrylate of di-lower alkyl-amino alkyl or the acrylate or methacrylate of di-lower alkyl amino hydroxyalkyl; and (3) optionally another vinyl monomer copolymerizable with the vinylpyrrolidone. Taking 100% as the molar basis, the units of vinylpyrrolidone represent from 20-99%, the units attributable to the acrylate or methacrylate represent between 1 and 80% and the units attributable to the other copolymerizable vinyl monomer represent between 0 and 50%.

Representative acrylates or methacrylates usefully employed in the production of such copolymers are principally the following: dimethylaminomethyl acrylate, dimethylaminomethyl methacrylate, diethylaminomethyl acrylate, diethylaminomethyl methacrylate, dimethylaminoethyl acrylate, dimethylaminoethyl methacrylate, dimethylamino-2-hydroxypropyl acrylate, dimethylamino-2-hydroxypropyl methacrylate, diethylamino-2-hydroxyethyl acrylate, diethylamino-2-hydroxyethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate and diethylaminooctyl acrylate.

The molecular weight of these copolymers is generally between 15,000 and 1,000,000 and more particularly between 50,000 and 500,000.

Representative of such copolymers are copolymers known under the commercial name of GAFQUAT 734 and 755, sold by GAF. The average molecular weight of GAFQUAT 734 is about 100,000 and that of GAFQUAT 755 is greater than 1,000,000.

3. Copolymers of the general formula

—A—Z—A—Z—A—Z— wherein

A represents a radical containing two secondary amine functions, preferably a radical derived from a heterocycle containing two secondary amine functions, e.g. the radical

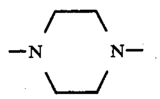

and

Z represents a divalent radical B or B′ wherein B and B′, identical or different, represent a straight or branched chain alkylene having up to 6 carbon atoms in the principal chain and also able to carry oxygen, nitrogen and/or sulfur atoms and from 1–3 aromatic or heterocyclic rings the oxygen, nitrogen and sulfur atoms can be present in the form of ether, thioether, sulfoxide, sulfone, sulfonium, amine, amine oxide, quaternary ammonium, amide, imide, urea, alcohol, ester and/or urethane groups.

These copolymers can be quaternized by lower alkyl or lower alkyl phenyl groups, principally, methyl, ethyl or benzyl groups.

The quaternization can be effected, for instance, with the aid of known quaternization agents such as, for example, lower alkyl chloride, bromide, iodide, sulfate, mesylate or tosylae or benzyl chloride or bromide.

These copolymers have an average molecular weight generally between 1000 and 15,000.

Representative of these copolymers are, in particular, those obtained by the polycondensation of piperazine and epichlorohydrin. The molar proportion of piperazine to epichlorohydrin can vary, for instance, from 0.5:2 to 2:0.5. These polycondensates can also be quaternized by lower alkyl or lower alkyl phenyl radicals as indicated above.

Such copolymers are described in U.S. Pat. No. 3,917,817, incorporated herein by reference.

The cationic surfactant which is suitable for use in this invention includes a cationic quaternary ammonium compound such as stearly dimethyl benzyl ammonium chloride, cetyl pyridinium chloride, cetyl trimethyl ammonium chloride, distearyl dimethyl ammonium chloride, dimethyl di(hydrogenated tollow) ammonium chloride, dimethyl difatty ammonium chloride, quaternized lanolin fatty acid amide, quaternary ammonium chloride derivates of polypropoxy tertiary amines, such as polyoxypropylene (9) methyl diethyl ammonium chloride, quaternized amides of ethylenediamine, quaternized amides of polyethyleneimine, alkyl morpholinium salts, alkyl imidazolinium salts, sulphonium salts, phosphonium salts, quaternized diamine salts, and the like.

The primary emulsifier suitable for use in this invention includes fatty acid esters and polyol esters of fatty acids such as glycerol monostearate, propylene glycol monostearate, ethylene glycol monostearate, and the like.

The secondary emulsifiers which may be used in this invention include the aliphatic alcohols of 16–18 carbon atoms, such as cetyl alcohol; polyethylene glycol fatty acid esters, and lanolin derivatives.

The surface active antistatic agents useful in the composition of this invention frequently belong to the class of nonionic surfactants. These include fatty esters of sorbitol, fatty esters of sorbitol condensed with ethylene oxide, ethoxylated fatty alcohols, ethoxylated fatty acids, ethoxylated fatty amines, ethoxylates of synthetic alcohols, and the like. The preferred antistatic agent is N-cetyl-N-ethyl-morpholinium ethosulfate.

The preservative which may be used in this invention includes glutaraldehyde, formaldehyde, ethyl, methyl, propyl, and butyl hydroxybenzoate, alkyl cresols, dehydroacetic acid salts, benzyl alcohol, methyl paraben, 3-isothiazolinones, and the like, or mixtures thereof.

The composition of this invention may include other optional ingredients such as thickeners and viscosity modifiers such as polyethylene glycols, sodium chloride, ammonium chloride, sodium sulfate, carboxymethyl cellulose, hydroxyethyl cellulose, poly(ethylene oxide), polyvinyl alcohol, and ethyl alcohol; suspending agents such as magnesium/aluminum silicate; perfumes, dyes; opacifiers such as behenic acid, ethylene glycol mono or distearate and calcium stearate; sequestering agents such as the disodium salt of ethylenediamine tetra-acetic acid; buffers and builders such as citrates and phosphates; protein and/or protein derivatives; higher fatty acid alkanolamides such as the diethanolamides, di- or monisopropanolamides and monoethanolamides of fatty acids having about 10 to 14 carbons in the alkyl radical such as lauric, capric, myristic and coconut mono- and diethanolamides, and mixtures thereof.

The composition of this invention contains from about 0.1 to about 2.0 weight percent, preferably from about 0.5 to about 1.0 weight percent of the water soluble cationic polymer, from about 1 to about 8 weight percent, preferably from about 2 to about 5 weight percent of the cationic surfactant, and when used, from 0.01 to about 10 weight percent of one or more of the optional ingredients.

The compositions of this invention are prepared by merely mixing the various ingredients together in water.

The above composition is added to any water or aqueous solution used in processing the pelt or treating fur. Typical use concentrations may be attained by diluting the concentrate composition by about 100 fold. It may be added to a tanning, soaking or dyeing bath or it may be added to the water used in subsequent shaping, stretching or cleaning operations. It is applied by any suitable means to the pelt or fur being treated.

After treatment with the novel composition of the present invention, the fur hairs remain fluffy and firm as in their natural live state and have a texture and coloration strikingly similar to the texture and coloration of live fur.

The composition of this invention are particularly suitable for treating mink pelts or furs, particularly dyed mink and most particularly mink dyed black.

EXAMPLES

The following examples serve to give specific illustrations of the practice of this invention, but they are not intended in any way to limit the scope of this invention.

EXAMPLE 1

The following ingredients were mixed together:

| Ingredients | Percent by Weight |
|---|---|
| UCARE Polymer JR-30M[1] | 0.75 |
| Cetyl trimethyl ammonium chloride | 4.0 |
| Glutaraldehyde | 0.05 |
| Water | q.s. |

[1]A cationic cellulose resin sold by Union Carbide Corporation. It has a viscosity of 1,000-2,500 centipoise (a one percent solution measured on a Brookfield LVF, 30 rpm, spindle speed). It is prepared by the methods as described in the Example of U.S. Pat. No. 3,472,840.

The ingredients were mixed together in water at room temperature (about 25° C.).

EXAMPLE 2

The following composition was prepared as in Example 1:

| Ingredients | Percent by Weight |
|---|---|
| UCARE Polymer JR-400[2] | 1.0 |
| Stearyl dimethyl benzyl ammonium chloride | 3.0 |
| Cetyl alcohol | 1.0 |
| Glycerol monostearate | 1.0 |
| N—cetyl-N—ethyl-morpholinium ethosulfate | 0.5 |
| Glutaraldehyde | 0.05 |
| Water | q.s. |

[2]A cationic cellulose resin sold by Union Carbide Corporation. It has a viscosity of 300-500 centipoise (a one percent solution measured or a Brookfield LVF, 30 rpm. spindle speed). The resin is prepared by the methods as described in the Examples of U.S. Pat. No. 3,472,840.

EXAMPLE 3

The following composition was prepared as in Example 1:

| Ingredients | Percent by Weight |
|---|---|
| UCARE Polymer JR-400 | 0.75 |
| Stearyl dimethyl benzyl ammonium chloride | 3.0 |
| Cetyl alcohol | 1.0 |
| Glycerol monostearate | 1.0 |
| N—cetyl-N—ethyl-morpholinium ethosulfate | 0.5 |
| Glutaraldehyde | 0.05 |
| Water | q.s. |

EXAMPLE 4

The following composition was prepared as in Example 1:

| Ingredients | Percent by Weight |
|---|---|
| UCARE Polymer JR-400 | 1.0 |
| Dimethyl ditallow ammonium chloride | 3.0 |
| Glycerol monostearate | 1.0 |
| Cetyl alcohol | 1.0 |
| N—cetyl-N—ethyl morpholinium ethosulfate | 0.5 |
| Glutaraldehyde | 0.05 |
| Water | q.s. |

EXAMPLE 5

The following composition was prepared as in Example 1:

| Ingredients | Percent by Weight |
|---|---|
| UCARE Polymer JR-400 | 0.75 |
| Dimethyl ditallow ammonium chloride | 3.0 |
| Glycerol monostearate | 1.0 |
| Cetyl alcohol | 1.0 |
| N—cetyl-N—ethyl morpholinium ethosulfate | 0.5 |
| Glutaraldehyde | 0.05 |
| Water | q.s. |

The compositions of Examples 1 to 5 were used to treat mink pelts which had been dyed black. The compositions were diluted to contain 6 ounces of the composition in 5 gallons of water. The pelts were soaked in the diluted compositions for about 2 to 4 hours and dried in sawdust. The finished dried fur had a smooth, controlled appearance, felt soft and had improved sheen. Also, the treated skin remained supple and retained a soft feel.

What is claimed is:

1. A process for treating furred animal pelts and/or fur comprising applying to said pelts or fur an aqueous composition containing a water-soluble cationic polymer and a cationic surfactant, wherein said pelts or fur are soaked in a dilute solution of said composition for a time sufficient to produce a pelt or fur with a finished dried fur having a smooth, controlled appearance, soft feel and improved sheen, and a treated skin remaining supple and retaining a soft feel.

2. The process as defined in claim 1, wherein the water-soluble cationic polymer is a quaternized cellulose derivative.

3. The process as defined in claim 1, wherein the water-soluble cationic polymer is a synthetic polymer containing quaternary ammonium groups.

4. The process as defined in claim 1, wherein the cationic surfactant is a quaternary ammonium compound.

5. The process as defined in claim 1, wherein the aqueous composition additionally contains a primary emulsifier, a secondary emulsifer, a surface active antistatic agent and a preservative.

6. The process as defined in claim 1, wherein the furred animal pelt is a mink pelt.

7. A process for the treating furred animal pelts and/or fur comprising applying to said pelt or fur an aqueous composition containing a water-soluble cationic polymer and a cationic surfactant, wherein said pelts are soaked in a dilute solution of said composition for about 2 to 4 hours.

8. The process as defined in claim 7 wherein the water-soluble cationic polymer is a quaternized cellulose derivative.

9. The process as defined in claim 7 wherein the water-soluble cationic polymer is a synthetic polymer containing quaternary ammonium groups.

10. The process as defined in claim 7 wherein the cationic surfactant is a quaternary ammonium compound.

11. The process as defined in claim 7 wherein the aqueous composition additionally contains a primary emulsifier, a secondary emulsifier, a surface active antistatic agent and a preservative.

12. The process as defined in claim 7 wherein the furred animal pelt is a mink pelt.

* * * * *